US010286181B2

United States Patent
Mastrianni

(10) Patent No.: US 10,286,181 B2
(45) Date of Patent: May 14, 2019

(54) METHOD AND APPARATUS FOR VIRTUAL REALITY-BASED MINDFULNESS THERAPY

(71) Applicant: Cigna Intellectual Property, Inc., Wilmington, DE (US)

(72) Inventor: Steven J. Mastrianni, Unionville, CT (US)

(73) Assignee: Cigna Intellectual Property, Inc., Wilmington, DE (US)

( * ) Notice: Subject to any disclaimer, the term of this patent is extended or adjusted under 35 U.S.C. 154(b) by 491 days.

(21) Appl. No.: 15/134,706

(22) Filed: Apr. 21, 2016

(65) Prior Publication Data

US 2017/0189639 A1    Jul. 6, 2017

Related U.S. Application Data

(60) Provisional application No. 62/274,002, filed on Dec. 31, 2015.

(51) Int. Cl.
   *A61M 21/02* (2006.01)
   *A61M 21/00* (2006.01)

(52) U.S. Cl.
   CPC ....... *A61M 21/02* (2013.01); *A61M 2021/005* (2013.01); *A61M 2021/0027* (2013.01); *A61M 2205/3303* (2013.01); *A61M 2230/10* (2013.01)

(58) Field of Classification Search
   CPC ........ A61B 5/0482; A61B 5/048; A61B 5/486

USPC ...................................... 600/26–28; 128/897
   See application file for complete search history.

(56) References Cited

U.S. PATENT DOCUMENTS

| 4,987,896 | A  | * | 1/1991 | Nakamatsu | A47C 7/74 607/109 |
| 2002/0128540 | A1 | * | 9/2002 | Kim | A61B 5/486 600/301 |
| 2010/0010289 | A1 | * | 1/2010 | Clare | A61M 21/00 600/27 |

* cited by examiner

*Primary Examiner* — Samuel G Gilbert
(74) *Attorney, Agent, or Firm* — Morgan, Lewis & Bockius LLP

(57) ABSTRACT

In one embodiment, there is a computer-implemented method for delivering therapy to a user, comprising: providing data representative of an initial sensory stimulus to a sensory stimulus device and causing the sensory stimulus device to provide the initial sensory stimulus to the user; receiving alpha wave biometric data of the user from a brain electrical activity sensor while the sensory stimulus device provides the initial sensory stimulus; determining whether the alpha wave biometric data meets sensory stimulus adjustment criteria; if the alpha wave biometric data meets sensory stimulus adjustment criteria, adjusting the sensory stimulus provided to the user by providing data representative of an adjusted sensory stimulus to the sensory stimulus device and causing the sensory stimulus device to provide the adjusted sensory stimulus; and if the alpha wave biometric data fails to meet sensory stimulus adjustment criteria, continue causing the sensory stimulus device to provide the initial sensory stimulus to the user.

16 Claims, 6 Drawing Sheets

METHOD AND APPARATUS FOR VIRTUAL REALITY-BASED MINDFULNESS THERAPY

CROSS-REFERENCE TO RELATED APPLICATIONS

This application claims the benefit of U.S. Provisional Patent Application No. 62/274,002, filed Dec. 31, 2015, entitled "Method and Apparatus for Virtual Reality-based Mindfulness Therapy", incorporated by reference herein in its entirety.

BACKGROUND

The present invention relates generally to systems and methods for the delivery of therapies, such as mindfulness therapies designed to identify and mitigate certain symptoms associated of stress or other stress-related or stress induced conditions.

SUMMARY

In one embodiment, there is an electronic device for delivering therapy to a user comprising: a sensory stimulus device configured to provide sensory stimulus to the user; a brain electrical activity sensor configured to sense alpha waves of the user and generate alpha wave biometric data; one or more memory units each operable to store at least one program; a processor communicatively coupled to the sensory stimulus device, the brain electrical activity sensor, and the one or more memory units. The processor is configured to provide data representative of an initial sensory stimulus to the sensory stimulus device and cause the sensory stimulus device to provide the initial sensory stimulus. The processor is configured to receive alpha wave biometric data of the user from the brain electrical activity sensor while the sensory stimulus device provides the initial sensory stimulus to the user. The processor is configured to determine whether the alpha wave biometric data meets sensory stimulus adjustment criteria. In accordance with a determination that the alpha wave biometric data meets sensory stimulus adjustment criteria, the processor is configured to adjust the sensory stimulus provided to the user by providing data representative of an adjusted sensory stimulus to the sensory stimulus device and cause the sensory stimulus device to provide the adjusted sensory stimulus to the user. In accordance with a determination that the alpha wave biometric data fails to meet sensory stimulus adjustment criteria, the processor is configured to continue causing the sensory stimulus device to provide the initial sensory stimulus to the user.

In a further embodiment, the alpha wave biometric data includes data representing an alpha wave frequency, and the alpha wave frequency is about 7 hertz to about 12 hertz.

In a further embodiment, the sensory stimulus adjustment criteria include a criterion that is met when the alpha wave biometric data indicates a non-occurrence of alpha waves generated by the user.

In a further embodiment, the sensory stimulus adjustment criteria include a criterion that is met when the alpha wave biometric data indicates a decreased occurrence of alpha waves generated by the user as compared to a predetermined favorable alpha wave biometric data.

In a further embodiment, the sensory stimulus adjustment criteria include a criterion that is met when the alpha wave biometric data indicates a similar occurrence of alpha waves generated by the user as compared to a predetermined unfavorable alpha wave biometric data.

In a further embodiment, the alpha wave biometric data is first alpha wave biometric data, the processor is further configured to: receive second alpha wave biometric data of the user from the brain electrical activity sensor before providing data representative of the initial sensory stimulus to the sensory stimulus device; and determining whether the alpha wave biometric data meets sensory stimulus adjustment criteria includes comparing the first alpha wave biometric data to the second alpha wave biometric data.

In a further embodiment, the sensory stimulus adjustment criteria including a criterion that is met when the alpha wave biometric data indicates a similar occurrence of alpha waves generated by the user as compared to the second alpha wave biometric data.

In a further embodiment, the sensory stimulus device is a virtual reality headset.

In one embodiment, there is a computer-implemented method for delivering therapy to a user, comprising: providing data representative of an initial sensory stimulus to a sensory stimulus device configured to provide sensory stimulus to the user and cause the sensory stimulus device to provide the initial sensory stimulus to the user; receiving alpha wave biometric data of the user from a brain electrical activity sensor configured to sense alpha waves of the user while the sensory stimulus device provides the initial sensory stimulus to the user; and determining whether the alpha wave biometric data meets sensory stimulus adjustment criteria. In accordance with a determination that the alpha wave biometric data meets sensory stimulus adjustment criteria, the method further comprises adjusting the sensory stimulus provided to the user by providing data representative of an adjusted sensory stimulus to the sensory stimulus device and causing the sensory stimulus device to provide the adjusted sensory stimulus to the user. In accordance with a determination that the alpha wave biometric data fails to meet sensory stimulus adjustment criteria, the method further comprises continuing to cause the sensory stimulus device to provide the initial sensory stimulus to the user.

In a further embodiment, the alpha wave biometric data includes data representing an alpha wave frequency, and the alpha wave frequency is about 7 hertz to about 12 hertz.

In a further embodiment, the sensory stimulus adjustment criteria include a criterion that is met when the alpha wave biometric data indicates a non-occurrence of alpha waves generated by the user.

In a further embodiment, the sensory stimulus adjustment criteria include a criterion that is met when the alpha wave biometric data indicates a decreased occurrence of alpha waves generated by the user as compared to a predetermined favorable alpha wave biometric data.

In a further embodiment, the sensory stimulus adjustment criteria include a criterion that is met when the alpha wave biometric data indicates a similar occurrence of alpha waves generated by the user as compared to a predetermined unfavorable alpha wave biometric data.

In a further embodiment, the alpha wave biometric data is first alpha wave biometric data, the method further comprising: receiving second alpha wave biometric data of the user from the brain electrical activity sensor before providing data representative of the initial sensory stimulus to the sensory stimulus device; and determining whether the alpha wave biometric data meets sensory stimulus adjustment criteria includes comparing the first alpha wave biometric data to the second alpha wave biometric data.

In a further embodiment, the sensory stimulus adjustment criteria including a criterion that is met when the alpha wave biometric data indicates a similar occurrence of alpha waves generated by the user as compared to the second alpha wave biometric data.

In a further embodiment, the sensory stimulus device is a virtual reality headset.

BRIEF DESCRIPTION OF THE SEVERAL VIEWS OF THE DRAWINGS

The following detailed description of embodiments of the invention will be better understood when read in conjunction with the appended drawings of an exemplary embodiment. It should be understood, however, that the invention is not limited to the precise arrangements and instrumentalities shown.

In the drawings.

DETAILED DESCRIPTION

Figure 1:
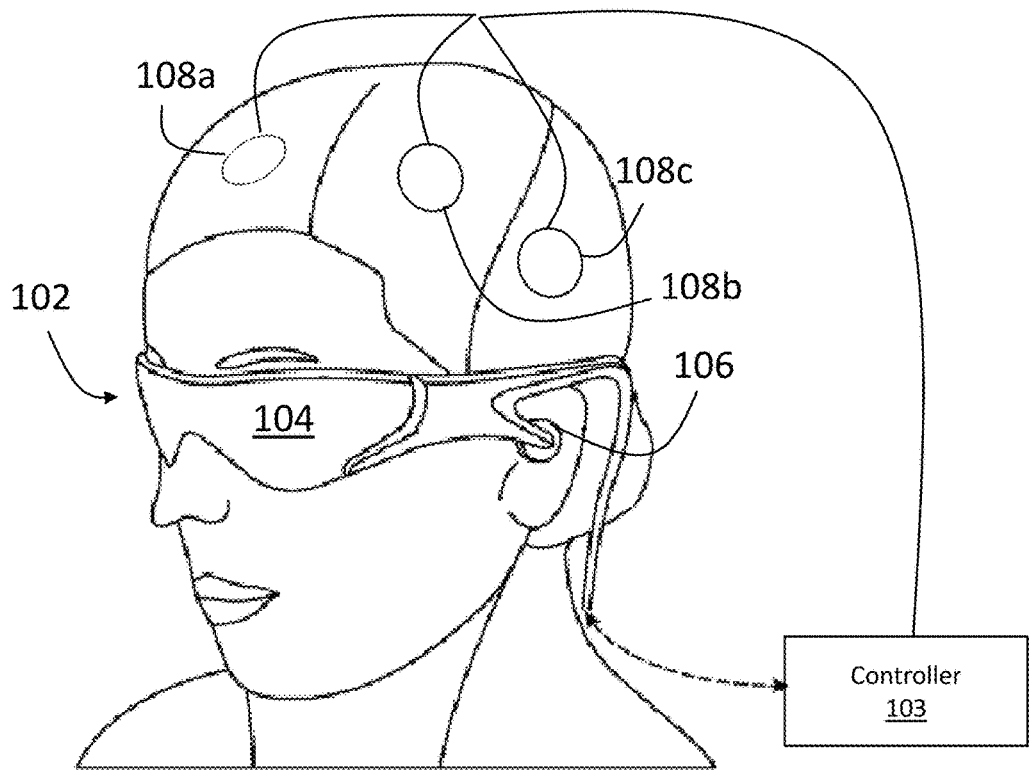
FIG. 1 illustrates an exemplary system of the present invention.

Referring to the drawings in detail, wherein like reference numerals indicate like elements throughout, there is shown in FIGS. 1-5 a system and method, generally designated, in accordance with an exemplary embodiment of the present invention.

Mindfulness is a state of active, open attention on the present. When you are mindful, you observe your thoughts and feelings from a distance, without judging them good or bad. Instead of letting your life pass you by, mindfulness means living in the moment and awakening to experience.

It has been discovered that therapies employing mindfulness can treat certain human ailments. For example, the treatment of stress using mindfulness therapies has been shown to significantly reduce the condition resulting in positive outcomes including improved productivity, fewer sick days, and better overall health.

The mindfulness therapies generally consist of a collection of various stimuli delivered to a user (i.e., subject). This content may consist of visual and audio experiences designed to elicit certain types of responses based on an initial selection of stimuli by the subject.

It is generally accepted that the treatment of stress or stress-related symptoms or conditions with traditional mindfulness therapies may cause some sort of retraining or rewiring of certain neural pathways, although this has not been scientifically proven. Similar types of therapies have been shown to help stroke victims regain normal speech abilities. What is known is that the level of concentration provided by intense meditation has been shown to be very effective in the treatment of stress and stress-related conditions.

One problem with traditional mindfulness therapies is that they use a "one size fits all" approach to treat certain human ailments such as stress. While these methods are effective for some, they may not be effective for others. This is because each person responds differently to these traditional therapies.

In certain embodiments of this invention, systems and methods are disclosed for the delivery of therapies that improve the efficacy of traditional therapies by dynamically altering the stimuli (therapy content) based on the subject's biometric feedback or other factors described in other embodiments of this invention.

For example, embodiments of the present invention, described herein, disclose a system and methods for the delivery of mindfulness therapies through a virtual reality headset that significantly intensifies the experience beyond more traditional audio or visual methods. These embodiments employ real time feedback to custom fit the therapies to the subject based on effectiveness, with that feedback being used to modify the content of the therapies to achieve the maximum effectiveness.

FIG. 1 illustrates an exemplary system of the present invention. In FIG. 1, a human machine interface 102 configured to deliver mindfulness therapy is provided to a user. To deliver therapy, the human machine interface 102 includes a controller 103 configured to provide a sensory stimulus, or a plurality of sensory stimuli, subsequently or simultaneously, to the user. The controller 103 is also configured to dynamically adjust the sensory stimulus based on user biometric data. As an example of sensory stimuli provided to a user, the human machine interface 102 depicted in FIG. 1 includes a visual display 104 coupled to the controller 103 to provide a visual and/or audio stimulus (e.g., visual and/or audio imagery of a tropical beach, an enchanted forest, or floating through outer space, or other stimuli selected based on a subject's social media interactions (e.g., displaying rock climbing stimuli if the subject posts about rock climbing on social media websites)) to the user. In some embodiments, the visual display 104 may be embedded in a headset, as shown in FIG. 1. In addition, the human machine interface 102 depicted in FIG. 1 may include audio speaker 106 coupled to the controller 103 for the controller 103 to provide an auditory stimulus to the user. In some embodiments, the audio speakers 106 may be embedded in earbuds (as shown in FIG. 1), headphones, or any other device capable of rendering or visualizing the auditory content of a stimuli.

In other embodiments, the human machine interface 102 may include other components (e.g., a fan, scented candles, chocolate) coupled to the controller 103 that produce other stimuli, including tactile stimulus, olfactory stimulus, and gustatory stimulus, to the user. For example, in some embodiments, an olfactory stimulus such as a scent drawn from nature, artificially or computer generated or controlled can be used to further enhance the virtual experience of the subject and thus improving the efficacy of the therapy.

In some embodiments, the human machine interface 102 may provide components (e.g., human-controlled inputs such as a mouse or keyboard) to facilitate the user's interaction or engagement with the stimuli. For example, the user may be interacting with or engaging stimuli such as web sites (e.g., social media) or other electronic sources that might help indicate the need for mindfulness therapy.

In some embodiments, the human machine interface 102 includes a virtual reality headset that implements a virtual reality program. Virtual reality headsets such as the OCULUS® MUSE® and MICROSOFT® HOLOLENS® have become popular with video gamer users because of their ability to deliver an immersive audio and visual experience; creating an environment where users feel like they're part of the game. Using the virtual reality headset in a mindfulness therapy application, a therapist may initially attempt to reduce stress of a user by configuring the human machine interface 102 to provide stimuli that attempts to relax a user. For example, the stimuli may be related to a relaxing beach setting. The human machine interface 102 may provide a visual stimulus by displaying a video that shows a white sandy beach in the foreground with a clear blue sky in the background. In addition, the human machine interface 102 may provide an auditory stimulus by providing the sound of waves crashing on the beach.

In some embodiments, the therapist may employ the present invention for the treatment or mitigation of the symptoms of Autism, PTSD, or any other type of malady that exists on the Autism scale.

In some embodiments, the human machine interface 102 includes inertial sensors to track user movement and orientation. In these embodiments, the user can look up, left, right, back, or down by naturally moving their head, while inertial sensors track the user movement and orientation. In some embodiments, the inertial sensors include one or more gyroscopes and accelerometers to track user movement and orientation and provide corresponding inertial sensor data. In response to receiving the inertial sensor data, the controller 103 is configured to recognize the direction and distance of user motion in each axis and provide an updated graphical image displayable on the visual display 104. This updated graphical image represents a real-time virtual view of a user in a virtual setting. In some embodiments, the controller 103 continually tracks the users' motion and continually updates the graphical images on the visual display 104 to correspond to the users' head orientation while a stimulus is provided to the user.

The ability to provide a virtual dynamic display to a user is helpful in mindfulness therapies. For example, in a mindfulness therapy using a beach setting, the user may be able to move his/her head and look around to enjoy the beach setting in 360 degree field of view.

The sensory stimulus (e.g., virtual reality) provided by a human machine interface can produce a physiological effect on a user. In tests performed on users wearing a virtual reality headset, the users experienced "real world" responses to a virtual reality stimulus. For example, when viewing a virtual roller coaster simulation, some users experienced nausea or dizziness normally associated with an actual roller coaster ride. These tests show that sensory information delivered as sensory stimulus by virtual reality headsets are every bit as realistic as when users actually experience the event simulated in virtual reality.

In some embodiments, the human machine interface 102 is configured to measure and collect biometric data of the user. In some applications, such as mindfulness therapy, it is advantageous to measure and collect biometric data of a user while an initial sensory stimulus is provided so that the stimuli can be adjusted, if necessary, to provide better therapy. In some embodiments, the subject may be presented with stimuli or scenarios designed to promote a neutral state, between relaxation and stress.

However, in some embodiments, the human machine interface 102 is configured to measure and collect biometric data of the user while no initial stimulus is provided. In these applications of mindfulness therapy, it is advantageous to measure and collect biometric data of a user while no sensory stimulus is provided so that the human machine interface 102 can obtain a baseline reading of the user's biometric data and then generate a stimulus accordingly. Then, when sensory stimulus is later provided, the human machine interface 102 can compare the initial baseline biometric data while no sensory stimulus is provided to the subsequent biometric data where sensory stimuli is provided to determine whether to adjust the provided sensory stimulus based on certain sensory stimulus adjustment criteria.

The ability to dynamically adjust (or generate) stimuli may be helpful because each user may respond differently to stimuli. By dynamically adjusting stimuli, each application of mindfulness therapy can be adjusted or tailored to the specific user. This improves upon traditional therapies with static stimuli where the traditional therapies may only work for a portion of the users because the stimuli remain unchanged, regardless of effectiveness or ineffectiveness. Also, by measuring and collecting biometric data, the controller 103 may implement machine learning applications that can process the biometric data to i) identify therapies that have generated desired outcomes (e.g., reduced stress levels) and/or ii) classify/rate the biometric data so that, in subsequent uses, the classification and/or rating data may be used to determine when to adjust the stimuli and provide better therapy.

In some embodiments, mindfulness therapies may be directed or specified by the subject's genomic data. Examples of genomic data may include inherited traits, genomic factors such as chromosomal data, or other data that describes the physiological aspects of the subject.

There are a number of different types of biometric data measured by the human machine interface 102. Examples may include heart rate, oxygen saturation ($SPO_2$), and blood pressure, among others. To measure biometric data of a user, the human machine interface 102 may include one or more wired or wireless biometric measuring devices including blood pressure cuffs or indicators, pulse oximeters, heart rate monitors, or any other transcutaneous or subcutaneous biometric sensor for the purpose of collecting or reading the biometric information associated with a user. Other examples of biometric data include user voice recordings. When measuring voice recordings, one or more wired or wireless biometric measuring devices may include a microphone or any other type of sound or voice recording device configured to measure user speech or utterance, including any of: a phoneme, phrase, tone, amplitude, or any other aspect of the subject's voice may be used to affect the scenario or outcome based on the desired target outcome or result.

In another example of biometric data, the human brain emits low amplitude (e.g., approximately 20-200 μV) signals related to certain forms of brain activity in response to stimuli. To measure brain activity, the human machine interface 102 may include one or more brain electrical activity sensors configured to detect the brain wave patterns (e.g., electrical activity of the brain) of the user. An example of a brain electrical activity sensor is an electroencephalogram (EEG) sensor (e.g., EEG sensors 108a, 108b and 108c). The brain electrical activity sensors may measure and collect brain wave data emitted from parts of the user's brain, including, but not limited to the hippocampus, occipital lobe, temporal lobe, frontal lobe, parietal lobe, limbic lobe, insular cortex, or any other part the brain that is capable of generating neural oscillations that can be collected and analyzed.

Figure 2A:
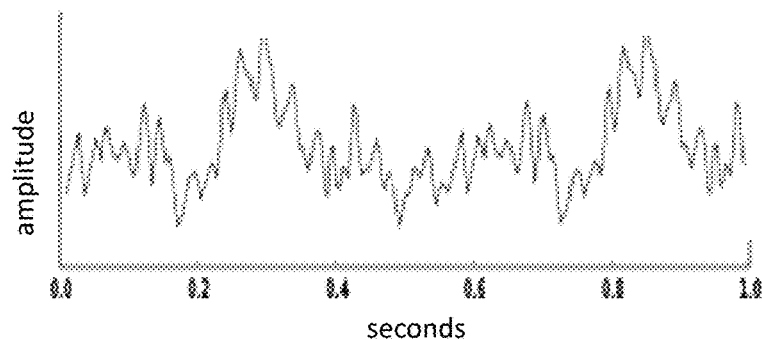
FIG. 2A shows a plot depicting an exemplary electrical signal representative of a typical nondescript electrical activity in the human brain.

In FIG. 2A, there is shown a plot depicting an exemplary electrical signal representative of a typical nondescript electrical activity in the human brain. The electrical activity shown in FIG. 2A may represent an EEG signal measured by the human machine interface 102. In some embodiments, the human machine interface 102 may filter the EEG signal to extract the different brain wave types apparent in a brain wave. These brain wave types are classified based on the frequency range.

FIGS. 2B-2F show exemplary plots of exemplary brain wave types including delta waves, theta waves, alpha waves, beta waves and gamma waves.

Figure 2B:
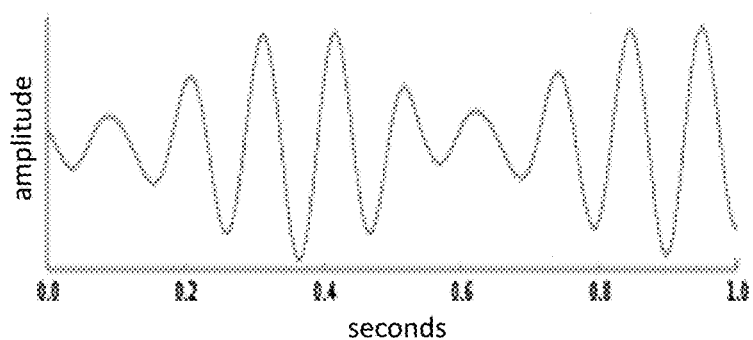
FIGS. 2B-2F show exemplary plots of exemplary brain wave types including delta waves, theta waves, alpha waves, beta waves and gamma waves.

In FIG. 2B, there is shown a plot depicting an exemplary electrical signal representative of alpha wave electrical activity in the human brain. Alpha waves have a frequency ranging from about seven hertz (7) to about twelve (12) hertz. Generally, alpha waves represent heighten imagination, visualization, memory, learning and concentration. These waves can be used to analyze how relaxed the brain is. If a user experiences an overload of stress and tension, the user probably has a reduced or decreased occurrence of alpha wave activity as compared to a predetermined favorable alpha wave activity level or a similar occurrence of alpha wave activity as compared to a predetermined unfavorable alpha wave activity level. On the contrary, if the user experiences low stress and tension levels, the user probably has a higher occurrence of alpha wave activity compared to a predetermined reference alpha wave activity. In some embodiments, the low occurrence of alpha wave activity represents unfavorable (non-relaxed) biometric data while the high occurrence of alpha wave activity represents favorable biometric data.

Figure 2C:
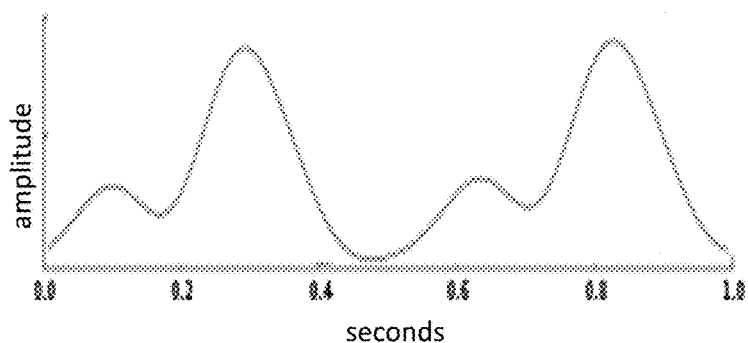

FIG. 2C shows a plot depicting an exemplary electrical signal representative of delta wave electrical activity in the human brain. Delta waves generally have a frequency ranging from about zero (0) hertz to about four (4) hertz. In the delta stage (i.e., while a person is in a deep sleep), the healing, rejuvenating and regeneration processes accelerate. These delta waves are generally not used while a user is awake because of limited electrical activity.

Figure 2D:
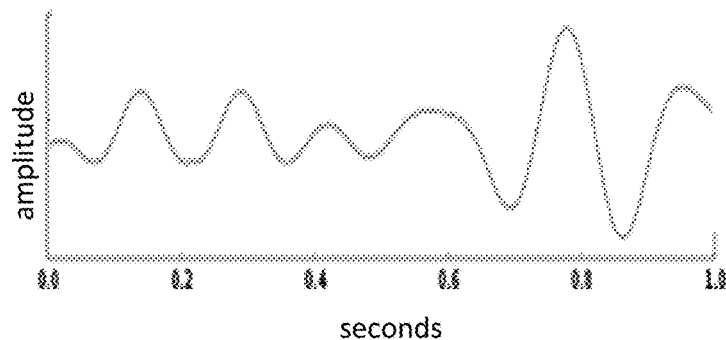

FIG. 2D shows a plot depicting an exemplary electrical signal representative of theta wave electrical activity in the human brain. Theta waves generally have a frequency ranging from about four (4) hertz to about seven (7) hertz. In the theta stage, ideas, visualizations and suggestion are more likely to enter the subconscious mind. Theta waves are mostly present during sleep and can be used to tell us how tired someone is.

Figure 2E:
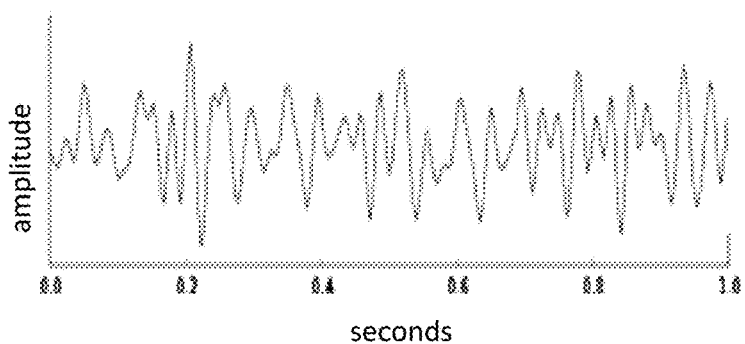

FIG. 2E shows a plot depicting an exemplary electrical signal representative of beta wave electrical activity in the human brain. Beta waves generally have a frequency ranging from about thirteen (13) hertz to about forty (40) hertz. High beta waves indicate increased stress, anxiety and "over-thinking". On the physical level, high brainwave beta frequency may cause hypertension, increased heart rate, increased blood flow, cortisone production and glucose consumption in a user.

Figure 2F:
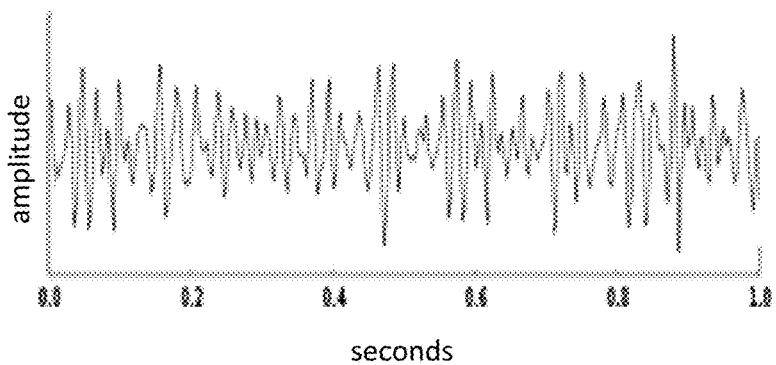

FIG. 2F shows a plot depicting an exemplary electrical signal representative of gamma wave electrical activity in the human brain. Gamma waves generally have a frequency ranging from about forty (40) hertz to about one hundred (100) hertz. Gamma waves are generally associated with peak concentration and extremely high levels of cognitive functioning and are related to peak mental and physical performance. Users with very high levels of gamma are usually intelligent, have an excellent memory, are happy and have strong self-control.

In some embodiments, the human machine interface 102 analyzes the biometric data to evaluate the impact of the therapy and determine whether the therapy is effective. Analyzing the biometric data may include determining whether the biometric data is favorable (e.g., the data indicates that a user's stress level is reduced or eliminated), or unfavorable (e.g., the data indicates a user's stress level remains at an undesired level).

The human machine interface 102 either maintains or alters the stimuli based on the determination whether the biometric data meets sensory stimulus adjustment criteria (e.g., whether the biometric data is favorable or unfavorable). If the biometric data is favorable, such that the biometric data does not meet sensory stimulus adjustment criteria, the human machine interface 102 is configured to continue or maintain the sensory stimuli provided to the user. If the biometric data is unfavorable, such that the biometric data meets sensory stimulus adjustment criteria, the human machine interface 102 is configured to adjust or modify the sensory stimuli provided to the user to improve the efficacy of the mindfulness therapy. By adjusting or modifying the sensory stimuli, the human machine interface 102 can alter the physiological effect on the user caused by the initial sensory stimulus. In mindfulness therapy applications, certain human ailments (e.g., stress) can be reduced by measuring certain unfavorable biometric data representing a human ailment during an initial sensory stimulus and adjusting the subsequent sensory stimulus to reduce or minimize the effects of the human ailment.

In some embodiments, the human machine interface 102 determines whether to maintain or alter the stimuli to the patient based on sensory stimulus adjustment criteria. In some embodiments, the sensory stimulus adjustment criteria includes the occurrence of alpha wave electrical activity in a user's brain. In some embodiments, the human machine interface 102 determines whether the measured biometric data representing alpha waves is favorable or unfavorable by comparing a characteristic of the measured biometric data to an activity threshold. In some embodiments, the activity threshold may delineate the occurrence (i.e., occurrence or non-occurrence) of alpha waves. In some embodiments, the activity threshold may delineate the prevalence (i.e., more prevalent, less prevalent), incidence level (i.e., higher incidence, lower incidence), and/or likelihood (i.e., higher likelihood, lower likelihood) of alpha waves as compared to other brain waves (e.g., beta, gamma).

In one embodiment, the human machine interface 102 samples the biometric data over a time period and averages the frequency characteristics of the biometric data to generate derived biometric data. Then, the human machine interface 102 determines whether sensory stimulus adjustment criteria are met by comparing the derived biometric data to the activity threshold.

If the derived biometric data exceeds the threshold, then the human machine interface 102 determines that the alpha wave biometric data is favorable (i.e., the occurrence of alpha waves, or the higher prevalence, incidence, or likelihood of alpha waves as compared to other brain waves). If the derived biometric data does not exceed the threshold, then the human machine interface 102 determines that the alpha wave biometric data is unfavorable (i.e., the non-occurrence of alpha waves, or the lower prevalence, incidence, or likelihood of alpha waves as compared to other brain waves). Then, using similar techniques discussed herein, the human machine interface 102 either continues or modifies the mindfulness therapy for the user accordingly.

While some embodiments use alpha wave biometric data to determine whether to modify therapy provided to a user, in other embodiments, other brain wave biometric data (e.g., delta wave, theta wave, beta wave and gamma wave) may be used for similar purposes described herein.

Also, while some embodiments use threshold techniques to determine whether biometric data is favorable or unfavorable, other techniques such as correlation may be used for similar purposes described herein. For example, the measured biometric data is compared to a predetermined favorable brain wave and a predetermined unfavorable brain wave using correlation techniques. The human machine interface 102 then determines whether the therapy is effective based on the most closely correlated outcome (i.e., favorable or unfavorable).

In some embodiments, the human machine interface 102 may correlate biometric data from the brain electrical activity sensors with biometric data from other sensors (e.g., blood pressure cuff, pulse oximeter) and compute a therapy efficacy value representing the efficacy of the particular therapy. Based on the computed therapy efficacy value, the human machine interface 102 may determine that the biometric data is favorable and maintain the current stimuli or determine that the biometric data is unfavorable and adjust the current stimuli to improve efficacy of the therapy. In some embodiments, the human machine interface 102 computes the therapy efficacy value by performing a weighted statistical analysis of the biometric data from each sensor to compute the therapy efficacy value. The human machine interface 102 can then modify the stimulus applied to the subject based on the therapy efficacy value. For example, the human machine interface 102 may apply a particular stimulus associated with or related to certain therapy efficacy values that have over time shown to be effective in a specific treatment. Those associations or relationships can be changed or modified over time to customize the stimulus for each subject. In some embodiments, these associations or relationships may be based on the subject's initial preferences, likes, dislikes, or other factors such as social media engagements or activities.

There are a few different methods for altering sensory stimuli once it is determined that the biometric data is unfavorable. In some embodiments, the human machine interface 102 may adjust the sensory stimuli by replacing a first stimulus (e.g., auditory stimulus) with a second stimulus (e.g., tactile stimulus). For example, in a mindfulness therapy application where a stimulus is the sound of waves crashing on the beach, this stimulus may be replaced by a tactile stimulus simulating a light breeze generated by a fan (i.e., a stimulus component of the human machine interface 102, in one embodiment).

In some embodiments, the human machine interface 102 may adjust one or more characteristics of a sensor stimulus to affect a desired result (e.g., reduce stress, improve attention or relaxation, improve alpha wave levels) on the user. Examples of sensor stimulus characteristics may include the volume level of an auditory stimulus, the language heard in an auditory stimulus, the foreground or background color of a visual stimulus, and the color of a particular object (e.g., figure, character, letter) in a visual stimulus, among others. For example, in a mindfulness therapy application where the stimulus is a visual stimulus of displaying a video that shows a white sandy beach in the foreground with a blue sky with a few clouds in the background, a characteristic of the stimulus, such as the blue sky with a few clouds, may be replaced with a clear blue sky.

In some embodiments, the human machine interface 102 may adjust the sensory stimuli by adding a second stimulus (e.g., auditory stimulus) to a first stimulus (e.g., tactile stimulus). For example, in a mindfulness therapy application where a first stimulus is the sound of waves crashing on the beach, a second stimulus may be added by a tactile stimulus simulating a light breeze generated by a fan (i.e., a stimulus component of the human machine interface 102, in one embodiment).

In some embodiments, the human machine interface 102 may adjust the sensory stimuli by removing a second stimulus (e.g., auditory stimulus) from a group of stimulus. For example, in a mindfulness therapy application where a first stimulus is the sound of waves crashing on the beach and a second stimulus is a tactile stimulus simulating a light breeze generated by a fan, the tactile stimulus may be removed.

In some embodiments, the human machine interface 102 may adjust the sensory stimuli by selecting a stimulus from a collection or repository of stimuli that have been known to generate certain desired outcomes based on the determination whether the biometric data is favorable or unfavorable. As each stimulus is executed and results are gathered, the repository is updated with the stimuli that have generated the desired or best outcome for the user. As a result, the repository stores a plurality of different stimuli that have been show to generate the best outcomes for a user. This form of machine learning continually observes the outcomes of specific therapies as applied by the human machine interface 102, or other human machine interfaces, and stores the stimuli in the repository where they are appropriately classified, rated, and made available for the purpose of dynamically adjusting a therapy.

In some embodiments, the human machine interface 102 may adjust the sensory stimuli by selecting a stimulus based on a subject's social media interactions (e.g., displaying rock climbing visual stimuli if the subject posts about rock climbing on social media websites).

Figure 3:
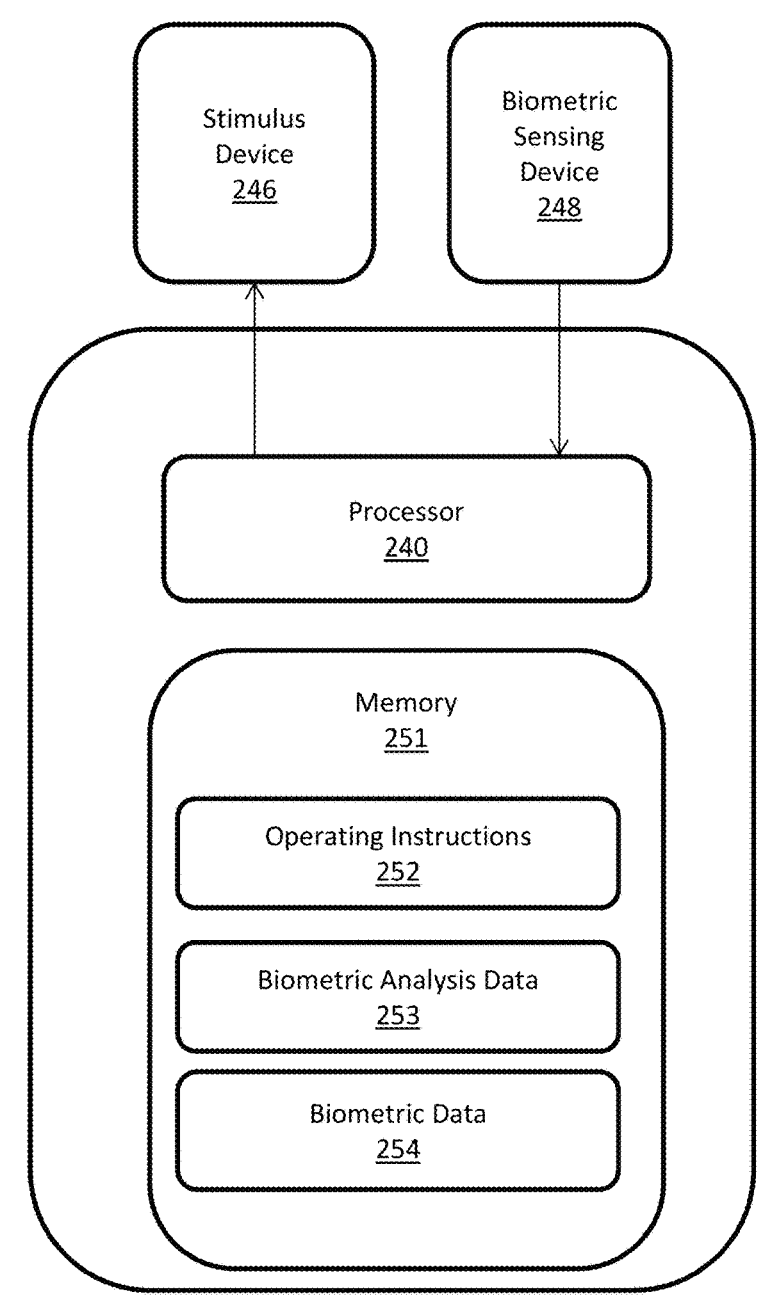
FIG. 3 illustrates components of the exemplary controller illustrated in FIG. 1.

FIG. 3 illustrates components of the exemplary controller 103 illustrated in FIG. 1. In this embodiment, the controller 103 includes control circuitry components including processor 240, and memory 241. The controller 103 is coupled to one or more stimulus devices (e.g., stimulus device 246) and/or one or more biometric sensing devices (e.g., biometric sensing device 248).

The stimulus devices are devices configured to provide sensory stimuli to the user. Examples of the sensory stimuli include the visual display 104 and audio speakers 106 shown in FIG. 1, among other sensory stimulus types described herein.

The biometric sensing devices are devices configured to measure biometric data of the patient. Examples of biometric sensing devices include the EEG sensors 108a, 108b and 108c shown in FIG. 1, among other biometric sensing device types described herein.

In some embodiments, the controller 103 is coupled to stimulus device 246 and/or biometric sensing device 248 via a wired connection or a wireless connection. The controller 103 communicates with stimulus device 246 and/or biometric sensing device 248 via a communication interface. A communication interface allows data to be transferred between controller 103 and stimulus device 246 and/or biometric sensing device 248. Examples of communication interfaces may include a modem, a network interface (such as an Ethernet card), and a communication port, by way of example. Data transferred via a communication interface are in the form of signals, which may be electronic, electromagnetic, optical, or other signals capable of being received by communication interface. These signals are provided to communication interface via a communication path. The communication path carries signals and may be implemented using wire or cable, fiber optics, a phone line, a wireless link, a cellular phone link, a radio frequency link, or any other suitable communication channel, including a combination of the foregoing exemplary channels.

Processor 240 is configured to transmit sensory stimulus to a user via stimulus device 246 and receive biometric sensing data from the biometric sensing device 248. As discussed herein, processor 240 is also configured to analyze the biometric sensing data and determine whether to alter the sensory stimuli provided to the user based on whether the biometric sensing data is favorable or unfavorable.

Memory 251 may include any volatile or non-volatile media, such as a random access memory (RAM), read only memory (ROM), non-volatile RAM (NVRAM), electrically erasable programmable ROM (EEPROM), flash memory, and the like. Memory 251 may store computer-readable instructions that, when executed by processor 240, cause processor 240 to perform various functions described herein. Memory 241 may include operating instructions 252 executable by the processor 240 for causing processor 240 to process biometric data and transmit certain sensory stimulus to a user using the functionality described herein. Memory 241 may also include biometric analysis data 253 related to stimuli that produce favorable or unfavorable biometrics in a user and/or biometric control data (e.g., predetermined thresholds, predetermined biometric data) used as a control for comparing to measured biometric data to determine therapy efficacy. Lastly, memory 241 may also include all biometric data 254 related to the biometric data measured by one or more biometric sensing devices.

Figure 4:
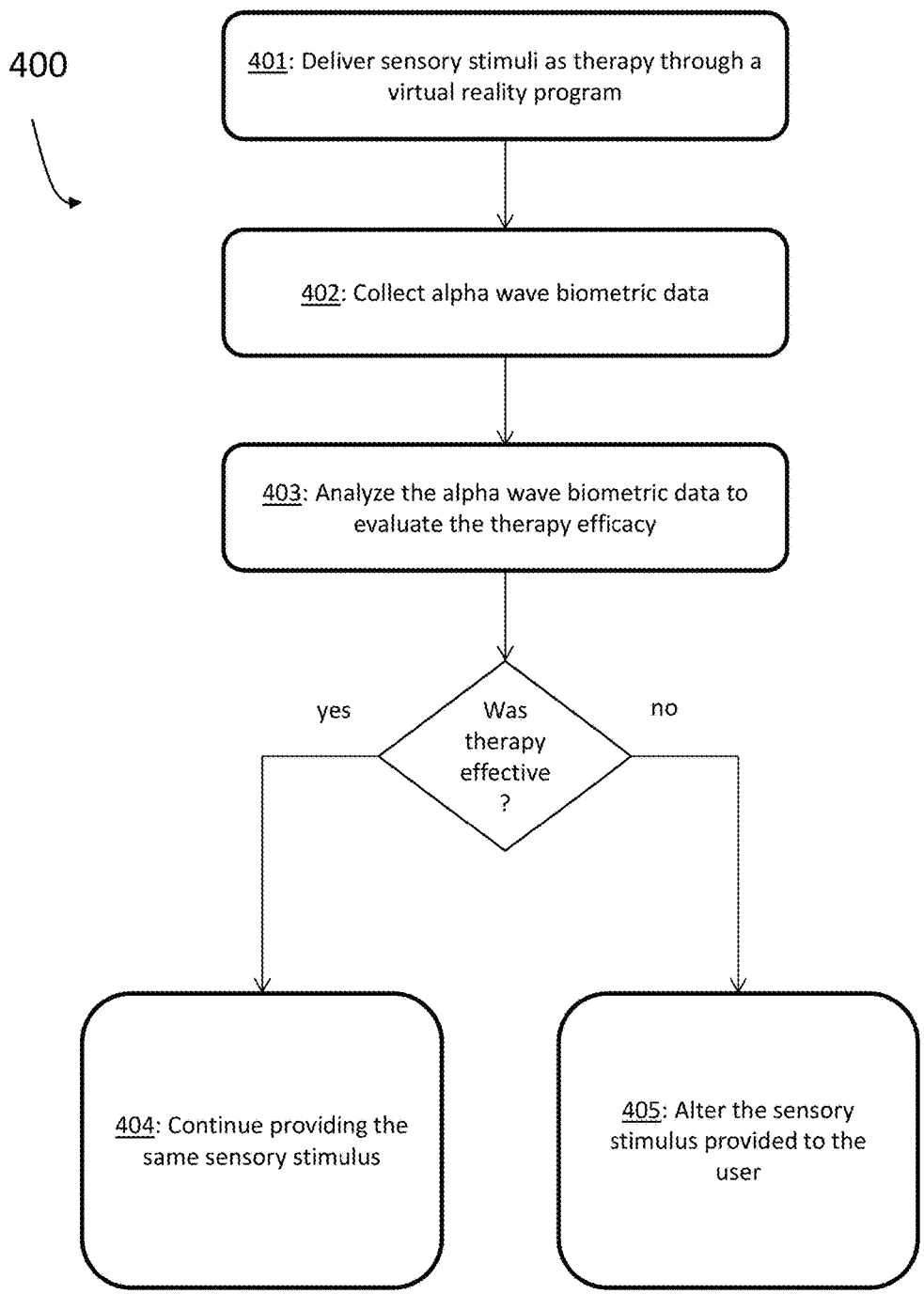
FIG. 4 illustrates an exemplary method according to at least one embodiment of the present invention.

FIG. 4 illustrates an exemplary method 400, according to at least one embodiment of the present invention.

In step 401, the controller 103 delivers sensory stimuli as therapy through a virtual reality program.

In step 402, the controller 103 collects alpha wave biometric data from a biometric sensor coupled to a user.

In step 403, the controller 103 analyzes the alpha wave biometric data to evaluate the therapy efficacy.

In step 404, if the therapy is effective, the controller 103 continues providing the same sensory stimulus.

In step 405, if the therapy is ineffective, the controller 103 alters the sensory stimulus provided to the user.

Figure 5:
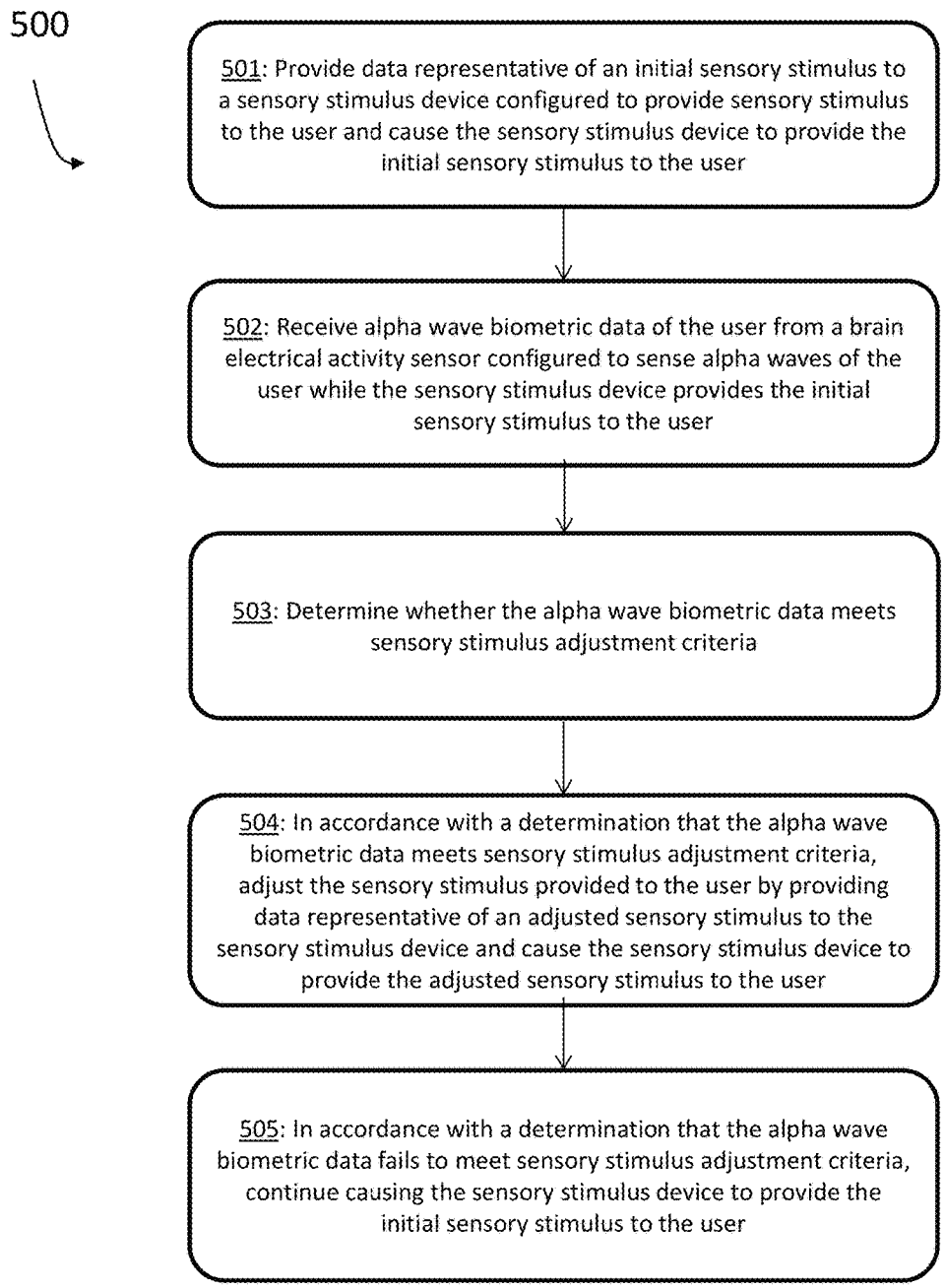
FIG. 5 illustrates an exemplary method according to at least one embodiment of the present invention.

FIG. 5 illustrates an exemplary method 500, according to at least one embodiment of the present invention.

In step 501, the controller 103 provides data representative of an initial sensory stimulus to a sensory stimulus device (e.g., stimulus device 246) configured to provide sensory stimulus to the user and causing the sensory stimulus device to provide the initial sensory stimulus to the user.

In step 502, the controller 103 receives alpha wave biometric data of the user from a brain electrical activity sensor (e.g., biometric sensing device 248) configured to sense alpha waves of the user while the sensory stimulus device provides the initial sensory stimulus to the user.

In step 503, the controller 103 determines whether the alpha wave biometric data meets sensory stimulus adjustment criteria. In some embodiments, the sensory stimulus adjustment criteria including a criterion that is met when the alpha wave biometric data indicates a non-occurrence of alpha waves generated by the user. In some embodiments, the sensory stimulus adjustment criteria including a criterion that is met when the alpha wave biometric data indicates a decreased occurrence of alpha waves generated by the user as compared to a predetermined favorable alpha wave biometric data. In some embodiments, the sensory stimulus adjustment criteria including a criterion that is met when the alpha wave biometric data indicates a similar occurrence of alpha waves generated by the user as compared to a predetermined unfavorable alpha wave biometric data. In some embodiments, sensory stimulus adjustment criteria includes a criterion that is met when the alpha wave biometric data is similar to baseline alpha wave biometric data of the user before the initial sensory stimulus is provided to the user.

In step 504, in accordance with a determination that the alpha wave biometric data meets sensory stimulus adjustment criteria, the controller 103 adjusts the sensory stimulus provided to the user by providing data representative of an adjusted sensory stimulus to the sensory stimulus device and causes the sensory stimulus device to provide the adjusted sensory stimulus to the user.

In step 505, in accordance with a determination that the alpha wave biometric data fails to meet sensory stimulus adjustment criteria, the controller 103 continues causing the sensory stimulus device to provide the initial sensory stimulus to the user.

* * *

In at least one embodiment, there is included one or more computers having one or more processors and memory (e.g., one or more nonvolatile storage devices). In some embodiments, memory or computer readable storage medium of memory stores programs, modules and data structures, or a subset thereof for a processor to control and run the various systems and methods disclosed herein. In one embodiment, a non-transitory computer readable storage medium having stored thereon computer-executable instructions which, when executed by a processor, perform one or more of the methods disclosed herein.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. The words "right", "left", "lower" and "upper" designate directions in the drawings to which reference is made. The words "inwardly" and "outwardly" refer to directions toward and away from, respectively, the geometric center of the device. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

What is claimed is:

1. An electronic device for delivering therapy to a user comprising:
    a sensory stimulus device configured to provide a sensory stimulus to the user;
    a brain electrical activity sensor configured to sense alpha waves of the user and generate alpha wave biometric data;
    one or more memory units each operable to store at least one program;
    a processor communicatively coupled to the sensory stimulus device, the brain electrical activity sensor, and the one or more memory units, the processor configured to execute the at least one program that, when executed by the processor, causes the processor to:
        provide data representative of an initial sensory stimulus to the sensory stimulus device and cause the sensory stimulus device to provide the initial sensory stimulus;
        receive alpha wave biometric data of the user from the brain electrical activity sensor while the sensory stimulus device provides the initial sensory stimulus to the user;
        determine whether the alpha wave biometric data meets sensory stimulus adjustment criteria;
        in accordance with a determination that the alpha wave biometric data meets the sensory stimulus adjustment criteria, adjust the sensory stimulus provided to the user by providing data representative of an adjusted sensory stimulus to the sensory stimulus device and cause the sensory stimulus device to provide the adjusted sensory stimulus to the user; and
        in accordance with a determination that the alpha wave biometric data fails to meet the sensory stimulus adjustment criteria, continue causing the sensory stimulus device to provide the initial sensory stimulus to the user.

2. The electronic device of claim 1, wherein the alpha wave biometric data includes data representative of a frequency of an alpha wave of the user, and wherein the alpha wave frequency is 7 hertz to 12 hertz.

3. The electronic device of claim 1, wherein the sensory stimulus adjustment criteria including a criterion that is met when the alpha wave biometric data indicates a non-occurrence of alpha waves generated by the user.

4. The electronic device of claim 1, wherein the sensory stimulus adjustment criteria including a criterion that is met when the alpha wave biometric data indicates a decreased occurrence of alpha waves generated by the user as compared to a predetermined favorable alpha wave biometric data.

5. The electronic device of claim 1, wherein the sensory stimulus adjustment criteria including a criterion that is met when the alpha wave biometric data indicates a similar occurrence of alpha waves generated by the user as compared to a predetermined unfavorable alpha wave biometric data.

6. The electronic device of claim 1,
    wherein the alpha wave biometric data is first alpha wave biometric data,
    wherein the processor is further configured to: receive second alpha wave biometric data of the user from the brain electrical activity sensor before providing data representative of the initial sensory stimulus to the sensory stimulus device; and
    wherein determining whether the alpha wave biometric data meets the sensory stimulus adjustment criteria includes comparing the first alpha wave biometric data to the second alpha wave biometric data.

7. The electronic device of claim 6, wherein the sensory stimulus adjustment criteria including a criterion that is met when the alpha wave biometric data indicates a similar occurrence of alpha waves generated by the user as compared to the second alpha wave biometric data.

8. The electronic device of claim 1, wherein the sensory stimulus device is a virtual reality headset.

9. A computer-implemented method for delivering therapy to a user, comprising:
    providing data representative of an initial sensory stimulus to a sensory stimulus device configured to provide a sensory stimulus to the user and causing the sensory stimulus device to provide the initial sensory stimulus to the user;
    receiving alpha wave biometric data of the user from a brain electrical activity sensor configured to sense alpha waves of the user while the sensory stimulus device provides the initial sensory stimulus to the user;
    determining whether the alpha wave biometric data meets sensory stimulus adjustment criteria;
    in accordance with a determination that the alpha wave biometric data meets the sensory stimulus adjustment criteria, adjusting the sensory stimulus provided to the user by providing data representative of an adjusted sensory stimulus to the sensory stimulus device and causing the sensory stimulus device to provide the adjusted sensory stimulus to the user; and
    in accordance with a determination that the alpha wave biometric data fails to meet the sensory stimulus adjustment criteria, continue causing the sensory stimulus device to provide the initial sensory stimulus to the user.

10. The method of claim 9, wherein the alpha wave biometric data includes data representative of a frequency of an alpha wave of the user, and wherein the alpha wave frequency is 7 hertz to 12 hertz.

11. The method of claim 9, wherein the sensory stimulus adjustment criteria including a criterion that is met when the alpha wave biometric data indicates a non-occurrence of alpha waves generated by the user.

12. The method of claim 9, wherein the sensory stimulus adjustment criteria including a criterion that is met when the alpha wave biometric data indicates a decreased occurrence of alpha waves generated by the user as compared to a predetermined favorable alpha wave biometric data.

13. The method of claim 9, wherein the sensory stimulus adjustment criteria including a criterion that is met when the alpha wave biometric data indicates a similar occurrence of alpha waves generated by the user as compared to a predetermined unfavorable alpha wave biometric data.

14. The method of claim 9,
    wherein the alpha wave biometric data is first alpha wave biometric data,
    the method further comprising:
        receiving second alpha wave biometric data of the user from the brain electrical activity sensor before providing data representative of the initial sensory stimulus to the sensory stimulus device; and
    wherein determining whether the alpha wave biometric data meets the sensory stimulus adjustment criteria includes comparing the first alpha wave biometric data to the second alpha wave biometric data.

15. The method of claim 14, wherein the sensory stimulus adjustment criteria including a criterion that is met when the alpha wave biometric data indicates a similar occurrence of alpha waves generated by the user as compared to the second alpha wave biometric data.

16. The method of claim 9, wherein the sensory stimulus device is a virtual reality headset.

\* \* \* \* \*